United States Patent
Farina et al.

[11] Patent Number: 5,603,941
[45] Date of Patent: Feb. 18, 1997

[54] MULTIFUNCTIONAL BIODISPERSANT/BIOCIDAL COMPOSITIONS

[75] Inventors: Thomas E. Farina, Flemington, N.J.; Frank J. Himpler, Easton, Pa.; J. Steven Colby, New Providence, N.J.

[73] Assignee: Lonza, Inc., Annandale, N.J.

[21] Appl. No.: 237,032

[22] Filed: May 3, 1994

[51] Int. Cl.⁶ ............................................. A01N 25/34
[52] U.S. Cl. ................................. 424/405; 424/408
[58] Field of Search ......................... 424/409, 405, 424/408

[56] References Cited

U.S. PATENT DOCUMENTS

| | | | |
|---|---|---|---|
| 2,789,078 | 4/1957 | Trusler | 424/409 |
| 3,296,069 | 1/1967 | Kowalski | 424/632 |
| 3,412,021 | 11/1968 | Paterson | 210/667 |
| 3,520,976 | 7/1970 | Buckman et al. | 514/367 |
| 4,058,618 | 11/1977 | Ovchinnikov et al. | 514/389 |
| 4,560,766 | 12/1985 | Girard et al. | 548/311 |
| 5,023,612 | 6/1991 | Buchan et al. | 25/181 |
| 5,063,213 | 11/1991 | Whitekettle et al. | 514/75 |

*Primary Examiner*—Peter F. Kulkosky
*Attorney, Agent, or Firm*—Darby & Darby

[57] ABSTRACT

According to the present invention, there are provided stable, solid compositions which include (a) a biodispersant, including surfactants; (b) a biocide, including halogenated hydantoins; and (c) optionally, a halogen scavenger, including a hydantoin; In a further embodiment, these compositions are added to a substrate in order to remove or to inhibit the formation of a biofilm and to prevent or to inhibit the growth of or to kill microorganisms.

39 Claims, No Drawings

MULTIFUNCTIONAL BIODISPERSANT/BIOCIDAL COMPOSITIONS

FIELD OF THE INVENTION

This invention relates to multifunctional, stable, solid compositions comprising a biodispersant, a biocide, and a halogen scavenger. This invention also relates to certain such multifunctional, stable, solid compositions which do not require a halogen scavenger when formulated with a substantially moisture-free halogenated biocide. These compositions permit the one step dispersement of both a biodispersant and a biocide in a substrate.

BACKGROUND OF THE INVENTION

Biodispersants are commonly used to inhibit the formation of or to remove biofilms. They are used in conjunction with biocides to provide general overall biocidal control. Biodispersants and biocides, particularly in solid forms, typically are not combined until they are applied to or dispersed in the substrate to be treated, especially if the biocide is an oxidizing biocide. This is because biodispersants and biocides, when in concentrated forms, generally are unstable in the presence of one another, each tending to decompose rapidly. Two part treatments are inconvenient, however, as they require storing, mixing, and measurement of each component.

Stable, solid compositions which include both a biodispersant and a biocide have now been discovered. These compositions overcome many of the disadvantages described above.

SUMMARY OF THE INVENTION

Bioeffective, stable, solid compositions have been discovered for the treatment of substrates that require both biodispersant and biocide treatment. These compositions can be formulated as compacted or tableted single administration unit forms. According to the present invention, there are provided stable, solid compositions comprising (a) at least one biodispersant, (b) at least one halogenated biocide, and (c) a halogen scavenger.

Also contemplated by the present invention are stable solid compositions comprising (a) at least one biodispersant and (b) at least one substantially moisture-free halogenated biocide.

In a further embodiment, these compositions are added to a substrate in order to remove or to inhibit the formation of a biofilm and to prevent or to inhibit the growth of or to kill microorganisms.

DETAILED DESCRIPTION OF THE INVENTION

Biodispersants are materials that remove or inhibit the formation of biofilms. They are used in conjunction with biocides to enhance overall biocidal control. Biodispersants are typically surfactants and preferably surfactants with some, but relative to a typical biocide slight, independent biocidal effects.

Any surfactants or biodispersants that are typically used in conjunction with oxidizing or non-oxidizing biocides are suitable for use in the present invention. Preferred biodispersants are those that are used in conjunction with oxidizing biocides. Furthermore, preferred biodispersants suitable for use in the present invention are in the solid form. Most preferred biodispersants are sulfosuccinate or sulfoacetate surfactants, including, but not limited to, sodium dioctylsulfosuccinate (SDSS), disodium lauryl sulfosuccinate, sodium lauryl sulfoacetate, or a combination thereof. SDSS biodispersant or surfactant is readily available under the trade name AEROSOL OT from American Cyanamid Company, Stamford, Conn. A preferred SDSS biodispersant is one in a powdered form comprising 85 percent by weight of SDSS and 15 percent by weight of sodium benzoate (AEROSOL OT-B).

Biocides are materials that prevent the growth of, inhibit the growth of, or kill microorganisms. Preferred biocides suitable for use in the present invention are in the solid form.

Biocides which are particularly suited for use in the present invention are halogenated biocides which generally can be divided into two classes, halogenated oxidizing biocides and halogenated non-oxidizing biocides. Halogenated oxidizing biocides are preferred for use in the present invention. Halogenated oxidizing biocides generally include, but are not limited to, bromine donor biocides, chlorine donor biocides, or bromine and chlorine donor biocides. Specific examples include, but are not limited to, alkali metal salts of dihalo cyanurates, such as sodium dichlorocyanurate, trichloroisocyanuric acid, various halogenated glycolurils, halogenated aromatic sulfonamides, alkali metal and alkaline earth hypochlorites such as sodium or calcium hypochlorite.

Most preferably, the biocides are dihalogenated. Dihalogenated hydantoins including, but not limited to dibromohydantoins; dichlorohydantoins; bromochlorohydantoins; or any combination thereof are most preferred. Special mention is made of dihalogenated di(lower alkyl) hydantoins of the formula

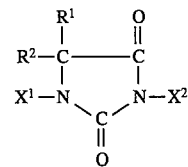

wherein $R^1$ and $R^2$ are independently methyl or ethyl and $X^1$ and $X^2$ are independently chlorine or bromine such as bromochloro-5,5-dimethylhydantoin. Certain of these biocides are further described in U.S. Pat. Nos. 4,560,766; 4,537,897; and 4,654,424.

Halgenated non-hydantoin biocides include but are not limited to, alkali metal salts of dihalo cyanurates, such as sodium dichlorocyanurate, trichloroisocyanuric acid, various halogenated glycolurils, halogenated aromatic sulfonamides, alkali metal and alkaline earth hypochlorites such as sodium or calcium hypochlorite.

If these preferred biocides are combined with biodispersants in the absence of halogen scavenger, the moisture content of the combination preferably should be less than about 0.1 weight percent, and biocides are substantially moisture-free if they contain about 0.1 or less weight percent of water.

Halogen scavengers are compounds capable of binding active halogen. Preferred halogen scavengers for use in the present invention are in the solid form. Preferred halogen scavengers are represented by the formula $RR^3NH$ wherein R and $R^3$ independently are carbonyl, sulfone, alkyl (preferably $C_1$–$C_4$ alkyl), aryl, or hydrogen. Most preferred halogen scavengers are represented by the formula

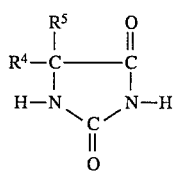

where $R^4$ and $R^5$ independently are methyl or ethyl including, but not limited to, heterocyclic compounds such as cyanuric acid and hydantoins such as, for example, 5,5-dimethylhydantoin and 5-ethyl-5-methylhydantoin. Particularly noteworthy are halogen scavengers which are di-lower alkylhydantoins including, but not limited to, dimethylhydantoins such as 5,5-dimethylhydantoin, mixed lower alkyl hydantoins including, but not limited to, 5-ethyl-5-methylhydantoin, or combinations thereof.

Destabilizing of a typical biodispersant/biocide solid mixture is usually evidenced by a change in color, an exotherm, and/or the evolution of a decomposition gas. Other indications of instability include tablet softening, swelling, or stickiness.

The unit forms of the present invention are solids and typically are compacted, compressed, or melted solids, including, but not limited to, tablets, briquettes, pucks, granules, or the like. The components typically are mixed in their solid forms to yield a dry blend by methods and means known to those skilled in the art. The dry blend can then be measured and formed into the unit form by means known to those in the art.

Preferably, a stable, solid composition according to the present invention will lose less than 0.5 percent by weight of free halogen per year. Typically, stability is observed by the absence of color change, gas evolution, and/or an exotherm in or from the composition.

The unit forms of the present invention comprise a biodispersing effective amount of the biodispersant, a biocidal effective amount of the biocide, and, if incorporated, a stabilizing amount of the halogen scavenger. A biodispersant effective amount of biodispersant is that amount sufficient to inhibit the formation of or to remove a biofilm. A biocidal effective amount of biocide is that amount sufficient to prevent or inhibit the growth of, or to kill microorganisms. A stabilizing amount of halogen scavenger is that amount sufficient to achieve the stability, as defined above, of a combination of biodispersant and biocide in solid form.

The precise amounts of biodispersant, biocide, and halogen scavenger in a composition that includes all three components will vary dependent upon the nature of each component. However, these compositions and unit forms preferably comprise from about 1 to about 30 parts by weight of biodispersant and from about 99 to about 70 parts by weight of biocide and halogen scavenger combined, based upon 100 parts by weight of biodispersant, biocide, and halogen scavenger combined; wherein the mole ratio of biocide to halogen scavenger ranges from about 0.5:1 to about 50:1. Most preferably, the solid, stable composition or unit form will comprise from about 5 to about 20 parts by weight of biodispersant and from about 95 to about 80 parts by weight of biocide and halogen scavenger combined, based upon 100 parts by weight of biodispersant, biocide, and halogen scavenger combined; wherein the mole ratio of biocide to halogen scavenger will range from about 0.5:1 to about 10:1.

Similarly the precise amounts of biodispersant and substantially moisture-free biocide in a composition that does not include the halogen scavenger will vary depending upon the mixture of each component. However, these compositions and unit forms preferably comprise from about 1 to about 30 parts by weight of biodispersant and from about 99 to about 70 parts by weight of substantially moisture-free biocide based upon 100 parts by weight of biodispersant and biocide combined. Most preferably, these compositions will comprise from about 5 to about 20 parts by weight of biodispersant and from about 95 to about 80 parts by weight of biocide based upon 100 parts by weight of biodispersant and biocide combined.

Any substrate susceptible to the formation of biofilms and/or the growth of microorganisms is suitable for treatment with the compositions of the present invention, particularly those in which the individual components will enter solution. These substrates include, but are not limited to, water and water systems and particularly water systems such as, for example, cooling water systems, air washers, toilets, and pools. The compositions of the present invention are added to the substrate by means known to those skilled in the art, such as by dispersing or dissolving the unit form in the substrate. Preferably, the amount of the unit forms described above are added in a combined biodispersing effective amount and a biocidal effective amount of form or stable, solid composition.

The unit forms of the present invention may include additives such as coloring agents, plasticizers, tableting or molding aids, disintegrants, or the like.

DESCRIPTION OF THE PREFERRED EMBODIMENTS

The following examples illustrate the invention without limitation. All parts and percentages are given by weight unless otherwise indicated.

Stability was determined by visual, olfactory, and/or tactile observation of color change, tablet softening, swelling, stickiness, evolution of halogen gas, and/or an exotherm.

EXAMPLE 1

A dry blend of 2.2 grams of biodispersant powder (85% SDSS, 15% sodium benzoate), 5 grams of biocide (a mixture of bromochloro-5,5-dimethylhydantoin; 1,3-dichloro-5,5-dimethylhydantoin; and 1,3-dichloro-5-ethyl-5-methylhydantoin) containing approximately 1 weight percent water, and 2.8 grams halogen scavenger (5,5-dimethylhydantoin) was tableted on a Carver tableting press under a pressure of 20,000 p.s.i.g. for 3 to 5 seconds.

The tablets were stored at room temperature and were observed for a period of time. The tablets were observed to be stable for over 3.5 months.

COMPARATIVE EXAMPLE 1A

A dry blend of 5 grams of a biodispersant powder (85% SDSS, 15% sodium benzoate) and 5 grams of biocide (a mixture of bromochloro-5,5 dimethylhydantoin; and 1,3-dichloro-5,5-dimethylhydantoin; 1,3-dichloro-5-ethyl-5-methylhydantoin containing approximately 1 weight percent of water) was tableted on a Carver tablet press at a pressure of 20,000 p.s.i.g. for 3 to 5 seconds.

The tablets were stored at room temperature and were observed. The tablets were observed to be stable for about 3 to 4 weeks at which point signs of decomposition were noted.

EXAMPLE 2

The procedure of Example 1 was followed, but the tablets were stored in an oven at 50° C. The tablets were observed to be stable for over 3.5 months.

COMPARATIVE EXAMPLE 2A

The procedure of Comparative Example 1A was followed, but the tablets were stored in an oven at 50° C. The tablets were observed to be stable for just over one week.

Examples 1 and 2, when compared with Comparative Examples 1A and 2A, demonstrate that compositions and unit forms according to the present invention exhibit enhanced stability at room temperature and at elevated temperatures.

EXAMPLE 3

A dry blend of 1 gram of biodispersant powder (85% SDSS, 15% sodium benzoate), 7 grams of biocide (a mixture of bromochloro-5,5-dimethylhydantoin; 1,3-dichloro-5,5-dimethylhydantoin; and 1,3-dichloro-5-ethyl-5-methylhydantoin containing about 1 weight percent of water), and 2 grams of 5,5-dimethylhydantoin was tableted on a Carver tablet press at a pressure of 20,000 p.s.i.g. for 3 to 5 seconds.

The tablets were stored in an oven at 50° C.

Results are illustrated in Table 1.

EXAMPLE 4

The procedure of Example 3 was followed substituting a dry blend of 2 grams of biodispersant powder (85% SDSS, 15% sodium benzoate), 6.2 grams of biocide (a mixture of bromochloro-5,5-dimethylhydantoin; 1,3-dichloro-5,5-dimethylhydantoin; and 1,3-dichloro-5-ethyl-5-methylhydantoin containing about 1 weight percent of water), and 1.8 grams of 5,5-dimethylhydantoin for the dry blend.

Results are illustrated in Table 1.

EXAMPLE 5

The procedure of Example 3 was followed substituting a dry blend of 1 gram of biodispersant powder (85% SDSS, 15% sodium benzoate), 7.6 grams of biocide (a mixture of bromochloro-5,5-dimethylhydantoin; 1,3-dichloro-5,5-dimethylhydantoin; and 1,3-dichloro-5-ethyl-5-methylhydantoin containing about 1 weight percent of water), and 1.4 grams of 5,5-dimethylhydantoin for the dry blend.

Results are illustrated in Table 1.

EXAMPLE 6

The procedure of Example 3 was followed substituting a dry blend of 2 grams of biodispersant powder (85% SDSS, 15% sodium benzoate), 6.7 grams of biocide (a mixture of bromochloro-5,5-dimethylhydantoin; 1,3-dichloro-5,5-dimethylhydantoin; and 1,3-dichloro-5-ethyl-5-methylhydantoin containing about 1 weight percent of water), and 1.3 grams of 5,5-dimethylhydantoin in the dry blend.

Results are illustrated in Table 1.

COMPARATIVE EXAMPLE 6A

The procedure of Example 3 was followed substituting a dry blend of 5 grams of biodispersant powder (85% SDSS, 15% sodium benzoate) and 5 grams of biocide (a mixture of bromochloro-5,5-dimethylhydantoin; 1,3-dichloro-5,5-dimethylhydantoin; and 1,3-dichloro-5-ethyl-5-methylhydantoin containing about 1 weight percent of water) for the dry blend.

Results are illustrated in Table 1.

TABLE 1

| | STABILITY AT 50° C. | | | | |
|---|---|---|---|---|---|
| Example | 3 | 4 | 5 | 6 | 6A |
| Biodispersant[a] (grams) | 1 | 2 | 1 | 2 | 5 |
| Biocide[b] (grams) | 7 | 6.2 | 7.6 | 6.7 | 5 |
| Halogen Scavenger (grams) | 2 | 1.8 | 1.4 | 1.3 | 0 |
| Molar Ratio Biocide/Halogen Scavenger | 2:1 | 2:1 | 3:1 | 3:1 | — |
| Stability (days) | >60 | >60 | 40 | 16 | 9 |

[a] - powder, 85% SDSS, 15% sodium benzoate.
[b] - mixture of bromochloro-5,5-dimethylhydantoin; 1,3-dichloro-5,5-dimethylhydantoin; and 1,3-dichloro-5-ethyl-5-methylhydantoin, containing about 1 weight percent of water.

Examples 3–6, when compared with Comparative Example 6A, demonstrate the enhanced stability of the unit forms of the present invention over the tableted biocide/biodispersant without the halogen scavenger.

EXAMPLE 7

A dry blend of 1.02 grams of biodispersant powder (85% SDSS, 15% sodium benzoate) and 9.03 grams of biocide (a mixture of bromochloro-5,5-dimethylhydantoin; 1,3-dichloro-5,5-dimethylhydantoin; and 1,3-dichloro-5-ethyl-5-methylhydantoin containing about 0.1 weight percent of water) was tableted on a Carver tableting press under a pressure of 20,000 p.s.i.g. for 3 to 5 seconds.

The tablets were stored in an oven at 50° C.

Results are illustrated in Table 2.

EXAMPLE 8

A dry blend of 1.03 grams of biodispersant powder (70% sodium lauryl sulfoacetate, 30% inerts) and 9.03 grams of biocide (a mixture of bromochloro-5,5-dimethylhydantoin; 1,3-dichloro-5,5-dimethylhydantoin; and 1,3-dichloro-5-ethyl-5-methylhydantoin containing about 0.1 weight percent of water) was tableted on a Carver tableting press under a pressure of 20,000 p.s.i.g. for 3 to 5 seconds.

The tablets were stored in an oven at 50° C.

Results are illustrated in Table 2.

EXAMPLE 9

A dry blend of 1.01 grams of biodispersant powder (85% disodium lauryl sulfosuccinate, 15% inerts) and 9.03 grams of biocide (a mixture of bromochloro-5,5-dimethylhydantoin; 1,3-dichloro-5,5-dimethylhydantoin; and 1,3-dichloro-5-ethyl-5-methylhydantoin containing about 0.1 weight percent of water) was tableted on a Carver tableting press under a pressure of 20,000 p.s.i.g. for 3 to 5 seconds.

The tablets were stored in an oven at 50° C.

Results are illustrated in Table 2.

TABLE 2

| | STABILITY AT 50° C. | | |
|---|---|---|---|
| | 7 | 8 | 9 |
| Biodispersant (grams) | 1.02[a] | 1.03[b] | 1.01[c] |
| Biocide[d] (grams) | 9.03 | 9.02 | 9.05 |
| Stability (Days) | >111 | >111 | >111 |
| Wt. % Biodispersant | 10 | 10 | 10 |

[a] - powder 85% SDSS, 15% sodium benzoate (Aerosol OT-B)
[b] - powder 70% sodium laurly sulfoacetate, 30% inerts (Lathanol LAL)
[c] - powder 85% disodium lauryl sulfosuccinate, 15% inerts (Monamate LA-100)
[d] - mixture of bromochloro-5,5-dimethyl hydantoin; 1,3-dichloro-5,5-dimethyl hydantoin, and 1,3-dichloro-5-ethyl-5-methyl hydantoin, containing less than 0.1 wt. % water.

Examples 7–9 demonstrate the stability of the unit forms of the present invention with a biocide having low moisture content and without halogen scavenger.

All patents and test methods mentioned above are hereby incorporated by reference.

Many variations of the present invention will suggest themselves to those skilled in the art in light of the above detailed description. Such obvious variations are within the full intended scope of the appended claims.

We claim:

1. A stable, solid composition comprising
   (a) a biodispersing effective amount of at least one biodispersant selected from the group consisting of sulfosuccinate surfactants, sulfoacetate surfactants, or any combination thereof;
   (b) a biocidal effective amount of at least one halogenated biocide compound; and
   (c) a stabilizing effective amount of at least one halogen scavenger selected from the group consisting of a compound having the formula $RR^3NH$ wherein R and $R^3$ are independently carbonyl, sulfone, alkyl, aryl, or halogen and a compound having the formula $$\begin{array}{c} R^5 \quad O \\ | \quad \| \\ R^4-C-----C \\ | \quad | \\ H-N \quad N-H \\ \diagdown C \diagup \\ \| \\ O \end{array}$$

where $R^4$ and $R^5$ independently are methyl or ethyl.

2. A stable, solid unit form comprising a composition as defined in claim 1.

3. A stable, solid unit form as defined in claim 2, wherein said unit form is compressed, compacted, or melted.

4. A stable, solid unit form as defined in claim 3, wherein said unit form is selected from the group consisting of a briquette, a tablet, a puck, and a granule.

5. A stable solid unit form as defined in claim 1, wherein said biodispersant is selected from the group consisting of sodium dioctylsulfosuccinate, disodium lauryl sulfosuccinate, sodium lauryl sulfoacetate, or a combination thereof.

6. A stable, solid unit form as defined in claim 1, wherein said halogenated biocide compound comprises an oxidizing biocide.

7. A stable, solid unit form as defined in claim 6, wherein said halogenated oxidizing biocide compound is selected from the group consisting of a solid bromine donor biocide, a solid chlorine donor biocide, or a combination thereof.

8. A stable, solid unit form as defined in claim 6, wherein said halogenated oxidizing biocide compound comprises at least one dihalogenated hydantoin.

9. A stable, solid unit form as defined in claim 8, wherein said dihalogenated hydantoin biocide compound is selected from the group consisting of dibromohydantoin, dichlorohydantoin, bromochlorohydantoin, or a combination of any of the foregoing.

10. A stable, solid unit form as defined in claim 6, wherein said halogenated oxidizing biocide compound comprises a compound having the formula $$\begin{array}{c} R^1 \quad O \\ | \quad \| \\ R^2-C-----C \\ | \quad | \\ X^1-N \quad N-X^2 \\ \diagdown C \diagup \\ \| \\ O \end{array}$$

wherein $R^1$ and $R^2$ independently are methyl or ethyl and $X^1$ and $X^2$ are independently chlorine or bromine.

11. A stable, solid unit form as defined in claim 10, wherein said oxidizing biocide compound is selected from the group consisting of bromochloro-5,5-dimethylhydantoin and bromochloro-5,5-dimethylhydantoin in combination with at least one other dihalogenated hydantoin.

12. A stable, solid unit form as defined in claim 1, wherein said halogen scavenger is selected from the group consisting of 5,5-dimethylhydantoin, 5-ethyl-5-methylhydantoin, or a combination thereof.

13. A stable, solid unit form comprising
   (a) a biodispersing effective amount of a sodium dioctylsulfosuccinate;
   (b) a biocidal effective amount of a mixture of dihalogenated hydantoins; and
   (c) a stabilizing effective amount of 5,5-dimethylhydantoin.

14. A stable, solid unit form as defined in claim 13, wherein said mixture of dihalogenated hydantoins includes bromochloro-5,5-dimethylhydantoin.

15. A stable, solid unit form as defined in claim 2, comprising from about 1 to about 30 parts by weight of (a) and from about 99 to about 70 parts by weight of (b) and (c) combined, based upon 100 parts by weight of (a), (b) and (c) combined; wherein the molar ratio of (b) to (c) ranges from about 0:5:1 to about 50:1.

16. A stable, solid unit form as defined in claim 15, comprising from about 5 to about 20 parts by weight of (a) and from about 95 to about 80 parts by weight of (b) and (c) combined, based upon 100 parts by weight of (a), (b), and (c) combined; wherein the molar ratio of (b) to (c) ranges from about 0:5 to about 10:1.

17. A stable, solid unit form comprising
   (a) from about 5 to about 20, parts by weight of sodium dioctylsulfosuccinate; and
   (b) from about 95 to 80 parts by weight of a mixture of
      (i) dihalogenated hydantoins containing bromochloro-5,5-dimethylhydantoin, and
      (ii) 5,5-dimethylhydantoin, combined; wherein the molar ratio of (i) to (ii) ranges from about 0:1 to about 10:1.

18. A method for removing or inhibiting the formation of a biofilm and for preventing or inhibiting the growth of or killing microorganisms in water systems comprising adding to said water a solid, stable unit form as defined in claim 2.

19. A stable, solid composition comprising (a) a biodispersing effective amount of at least one biodispersant selected from the group consisting of sulfosuccinate surfactants, sulfoacetate surfactants, or a combination thereof; and (b) a biocidal effective amount of at least one substantially moisture-free halogenated biocide compound.

20. A stable, solid unit form comprising a composition as defined in claim 19.

21. A stable, solid unit form as defined in claim 20, wherein said unit form is compressed, compacted, or melted.

22. A stable, solid unit form as defined in claim 21 wherein said unit form is selected from the group consisting of a briquette, a tablet, a puck, and a granule.

23. A stable solid unit form as defined in claim 19, wherein said biodispersant is selected from the group consisting of sodium dioctylsulfosuccinate, disodium lauryl sulfosuccinate, sodium lauryl sulfoacetate, or a combination thereof.

24. A stable, solid unit form as defined in claim 21, wherein said substantially moisture-free halogenated biocide compound comprises a halogenated oxidizing biocide.

25. A stable, solid unit form as defined in claim 24, wherein said substantially moisture-free halogenated oxidizing biocide compound is selected from the group consisting of a solid bromine donor biocide, a solid chlorine donor biocide, or a combination thereof.

26. A stable, solid unit form as defined in claim 25, wherein said substantially moisture-free halogenated oxidizing biocide compound comprises at least one dihalogenated hydantoin.

27. A stable, solid unit form as defined in claim 26, wherein said dihalogenated hydantoin biocide compound is selected from the group consisting of dibromohydantoin, dichlorohydantoin, bromochlorohydantoin, or a combination of any of the foregoing.

28. A stable, solid unit form as defined in claim 26, wherein said oxidizing biocide compound is selected from the group consisting of bromochloro-5,5-dimethylhydantoin and bromochloro-5,5-dimethylhydantoin in combination with at least one other dihalogenated hydantoin.

29. A stable, solid unit form as defined in claim 23, wherein said substantially moisture-free halogenated oxidizing biocide compound comprises a composition having the formula $$\begin{array}{c} R^1 \quad\quad O \\ | \quad\quad \| \\ R^2-C\!-\!-\!-\!-\!C \\ | \quad\quad | \\ X^1-N \quad\quad N-X^2 \\ \diagdown C \diagup \\ \| \\ O \end{array}$$

where $R^1$ and $R^2$ independently are methyl or ethyl and $X^1$ and $X^2$ are independently chlorine or bromine.

30. A stable, solid unit form comprising (a) a biodispersing effective amount of sodium dioctylsulfosuccinate; and (b) a biocidal effective amount of a substantially moisture-free mixture of dihalogenated hydantoins.

31. A stable, solid unit form as defined in claim 30, wherein said mixture of dihalogenated hydantoins includes bromochloro-5,5-dimethylhydantoin.

32. A stable, solid unit form as defined in claim 2, comprising from about 1 to about 30 parts by weight of (a) and from about 99 to about 70 parts by weight of (b), based upon 100 parts by weight of (a) and (b) combined.

33. A stable, solid unit form as defined in claim 32, comprising from about 5 to about 20 parts by weight of (a) and from about 95 to about 80 parts by weight of (b), based upon 100 parts by weight of (a) and (b) combined.

34. A stable, solid unit form comprising (a) from about 5 to about 20, parts by weight of sodium dioctylsulfosuccinate; and (b) from about 95 to 80 parts by weight of a substantially moisture-free mixture of dihalogenated hydantoins containing bromochloro-5,5-dimethylhydantoin.

35. A method for removing or inhibiting the formation of a biofilm and for preventing or inhibiting the growth of or killing microorganisms in water systems comprising adding to said water a solid, stable unit form as defined in claim 20.

36. A method for removing or inhibiting the formation of a biofilm and for preventing or inhibiting the growth of or killing microorganisms in a cooling water system, said method comprising adding to said cooling water system, a solid, stable unit form as defined in claim 20.

37. A method for removing or inhibiting the formation of a biofilm and for preventing or inhibiting the growth of or killing microorganisms in an air washer, said method comprising adding to said air washer, a solid, stable unit form as defined in claim 20.

38. A method for removing or inhibiting the formation of a biofilm and for preventing or inhibiting the growth of or killing microorganisms in a toilet, said method comprising adding to said toilet, a solid, stable unit form as defined in claim 20.

39. A method for removing or inhibiting the formation of a biofilm and for preventing or inhibiting the growth of or killing microorganisms in a pool, said method comprising adding to said pool, a solid, stable unit form as defined in claim 20.

* * * * *

UNITED STATES PATENT AND TRADEMARK OFFICE
CERTIFICATE OF CORRECTION

PATENT NO. : 5,603,941
DATED : Feb. 18, 1997
INVENTOR(S) : Thomas E. Farina, Frank J. Himpler, Steven Colby It is certified that error appears in the above-identified patent and that said Letters Patent is hereby corrected as shown below:

Claim 15, line 6: cancel "0:5:1" and substitute --0.5:1--.

Claim 16, line 6: Cancel "0:5" and substitute --0.5:1--.

Claim 17, line 8: cancel "0:1" and substitute --0.5:1--.

Signed and Sealed this

Twentieth Day of January, 1998

Attest:

BRUCE LEHMAN

*Attesting Officer*  *Commissioner of Patents and Trademarks*